United States Patent [19]
Tierney

[11] Patent Number: 5,954,685
[45] Date of Patent: Sep. 21, 1999

[54] ELECTROCHEMICAL SENSOR WITH DUAL PURPOSE ELECTRODE

[75] Inventor: Michael J. Tierney, San Jose, Calif.

[73] Assignee: Cygnus, Inc., Redwood City, Calif.

[21] Appl. No.: 08/653,161

[22] Filed: May 24, 1996

[51] Int. Cl.$^6$ .................................................... A61B 1/30
[52] U.S. Cl. ........................... 604/20; 600/573; 600/322; 600/347; 600/362
[58] Field of Search ..................................... 128/632, 635, 128/637, 639, 760; 604/20; 600/310, 322–323, 368, 573, 347, 355, 362

[56] References Cited

U.S. PATENT DOCUMENTS

| | | |
|---|---|---|
| 4,020,830 | 5/1977 | Johnson et al. . |
| 4,366,033 | 12/1982 | Richter et al. ........................... 128/635 |
| 4,457,748 | 7/1984 | Lattin et al. . |
| 4,474,570 | 10/1984 | Arivra et al. . |
| 4,477,971 | 10/1984 | Jacobsen et al. . |
| 4,633,879 | 1/1987 | Ong . |
| 4,702,732 | 10/1987 | Powers et al. . |
| 4,708,716 | 11/1987 | Sibalis . |
| 4,722,761 | 2/1988 | Cartmell et al. . |
| 4,731,049 | 3/1988 | Parsi . |
| 4,731,926 | 3/1988 | Sibalis . |

(List continued on next page.)

FOREIGN PATENT DOCUMENTS

| | | |
|---|---|---|
| 0 154 664 | 9/1985 | European Pat. Off. . |
| 0 304 304 | 2/1989 | European Pat. Off. . |
| 0 453 283 A1 | 10/1991 | European Pat. Off. . |
| A1 483883 | 6/1992 | European Pat. Off. . |
| 0 532 451 | 3/1993 | European Pat. Off. . |
| 62-133937 | 6/1987 | Japan . |
| WO 95/02357 | 1/1995 | WIPO . |
| WO 96/00109 | 1/1996 | WIPO . |
| Wo 96/00110 | 1/1996 | WIPO . |
| WO 97/02811 | 1/1997 | WIPO . |
| WO 97/24059 | 7/1997 | WIPO . |

OTHER PUBLICATIONS

U.S. Ser. No. 312,400, filed Sep.26, 1994.
U.S. application No. 08/526,732; Kurnik et al., filed Sep.5, 1995.
U.S. application No.08/527,061; Kurnik et al., filed Sep.12, 1995.
U.S. application No. 08/933,025; Tamada et al., filed Sep. 18, 1997.
U.S. application No. 08/680,719, Abraham et al., filed Jul. 11, 1996.
U.S. application No. 08/824,143; Kurnik et al., filed Mar. 25, 1997.
U.S. application No. 08/933,025, Kurnik et al., filed Sep. 18, 1997.
International Search Report for PCT/US95/07692 (Jun. 23, 1995).
Turner, A. P. F. et al., "Commercial perspectives for diagnostics using biosensors technologies," *ABL*, pp.10–18, published Nov. 1988.
Turner, A. P. F., "Diabetes Mellitus, Biosensors for Research and Management," *Biosensors*, vol.1, pp. 85–115, published by Elsevier, Ltd., London, U.K.

(List continued on next page.)

*Primary Examiner*—Mark Bockelman
*Attorney, Agent, or Firm*—Gary R. Fabian; Angela P. Horne; Barbara G. McClung

[57] ABSTRACT

The present invention provides an electrode assembly for use in a transdermal analyte sensor operating in an alternating polarity mode in which a single electrode element provides both the counter electrode and iontophoretic electrode functions. By combining both the functions of the iontophoretic and counter electrode, the surface area of the electrode with respect to each function may be made larger. In turn this increases the ability of the electrode to deliver the required electrical field over a larger area when operating in the iontophoretic mode as well as increasing the ability of the counter electrode to compensate for the larger sensing electrode facilitated by this new design.

18 Claims, 3 Drawing Sheets

U.S. PATENT DOCUMENTS

| | | |
|---|---|---|
| 4,865,582 | 9/1989 | Sibalis . |
| 4,883,457 | 11/1989 | Sibalis . |
| 4,919,770 | 4/1990 | Preidel et al. .......................... 128/635 |
| 4,953,552 | 9/1990 | DeMarzo . |
| 4,981,779 | 1/1991 | Wagner . |
| 4,986,271 | 1/1991 | Wilkins . |
| 5,001,054 | 3/1991 | Wagner . |
| 5,030,333 | 7/1991 | Clark, Jr. ............................... 128/635 |
| 5,036,861 | 8/1991 | Sembrowich et al. . |
| 5,050,604 | 9/1991 | Reshef et al. . |
| 5,050,612 | 9/1991 | Matsumura . |
| 5,069,908 | 12/1991 | Henley . |
| 5,076,273 | 12/1991 | Schoendorfer et al. . |
| 5,086,229 | 2/1992 | Rosenthal et al. . |
| 5,134,057 | 7/1992 | Tierney et al. . |
| 5,135,479 | 8/1992 | Sibalis et al. . |
| 5,135,480 | 8/1992 | Bannon et al. . |
| 5,139,023 | 8/1992 | Stanley et al. . |
| 5,140,985 | 8/1992 | Schroeder et al. ...................... 128/632 |
| 5,152,758 | 10/1992 | Kaetsu et al. ............................ 604/20 |
| 5,160,316 | 11/1992 | Henley ...................................... 604/20 |
| 5,161,532 | 11/1992 | Joseph . |
| 5,165,407 | 11/1992 | Wilson et al. . |
| 5,224,927 | 7/1993 | Tapper . |
| 5,224,928 | 7/1993 | Sibalis et al. . |
| 5,279,543 | 1/1994 | Glikfeld et al. . |
| 5,291,887 | 3/1994 | Stanley et al. . |
| 5,340,722 | 8/1994 | Wolfbeis et al. . |
| 5,356,632 | 10/1994 | Gross et al. . |
| 5,358,483 | 10/1994 | Sibalis . |
| 5,362,307 | 11/1994 | Guy et al. ................................. 604/20 |
| 5,364,346 | 11/1994 | Schrezenmeir . |
| 5,364,838 | 11/1994 | Robsamen . |
| 5,443,442 | 8/1995 | Phipps et al. ............................ 604/20 |
| 5,458,140 | 10/1995 | Eppstein et al. . |
| 5,460,177 | 10/1995 | Purdy et al. . |
| 5,497,772 | 3/1996 | Schulman et al. . |

OTHER PUBLICATIONS

Rao, G. et al, "Iontophoretic and Noninvasive Glucose Monitoring", *Controlled Release Society, Inc.*, Proceed. Intern. Symp. Control. Rel. Bioact. Mater., 21 (1994).

Santi, P., et al, "Reverse iontophoresis—Parameters determining electroosmotic flow: I. PH and ionic strength", *J. of Controlled Release*, 38, 1996, pp. 159–165.

Rao, G., et al, "Reverse Iontophoresis: Development of a Noninvasive Approach for Glucose Monitoring", *Pharmaceutical Research*, V. 10, No. 12, 1993, pp.1751–1755.

Tamada, J. A., et al., "Measurement of glucose in diabetic subjects using noninvasive transdermal extraction", *Nature Med.*, V. 1, No. 11, Nov. 1995, pp. 1198–1201.

Klonoff, D. C., "Noninvasive Blood Glucose Monitoring", *Diabetes Care*, V. 20, No. 3, Mar. 1997, pp. 433–437.

Boyce, N., "Searching for New, Noninvasive Ways to Monitor Blood Glucose", *Clin. Lab. News*, Feb. 1996/7.

"GLUCOWATCH™ A Painless, Automatic Glucose Monitor", Cygnus Corporate Mktg. Literature, Second Quarter, 1997.

Farinas, K. C., et al., "In Vitro Testing of a Non–Invasive Glucose Monitor", Technical Paper.

Conn, T. E., "Evolution of a Non–invasive Glucose Monitoring System for People with Diabetes", Technical Presentation, Mar. 1997.

Hunter, K. W., Jr., "Tekchnological Advances in Bedside Monitoring: Biosensors", *Arch Pathol Lab Med*, vol. 111, Jul. 1987, pp. 633–636.

Meyerhoff et al., "On Line Continuous Monitoring Of Subcutaneous Tissue Glucose In Men By combining Portable Glucosensor With Microdialysis", *Diabetologia* (1992) 35: 1087–1092.

Glikfeld, Peretz, et al, 1989, "Noninvasive sampling of biological fluids by iontophoresis", *Pharmaceutical Research* 6:988–990.

ELECTROCHEMICAL SENSOR WITH DUAL PURPOSE ELECTRODE

CROSS-REFERENCE TO OTHER APPLICATIONS

This application is related to co-pending earlier filed application Ser. No. 08/373,931, filed Jan. 10, 1995 entitled "Iontophoretic Sampling Device with Integrated Sensor" and earlier filed application Ser. No. 08/580,212, filed Dec. 28, 1995 entitled "Continuous Monitoring of Physiological Analytes" each of which applications are incorporated herein by reference in their entirety and which applications disclose inventions which were invented under an obligation to assign rights to the same entity as which the rights in the present invention were invented under an obligation to assign to.

FIELD OF THE INVENTION

The invention relates generally to the field of electrodes for electrochemical measurements, specifically electrodes used in the biomedical fields to measure concentrations of biomedically significant compounds.

BACKGROUND OF THE INVENTION

The measurement of internal body conditions through external measurements defines the art of medical diagnostics. It is a goal of medical diagnostic devices to be as minimally invasive as possible to achieve measurement of internal processes. Consequently, many devices have been designed which permit the measurement of bodily functions through electrical or electrochemical skin surface measurements.

The measurement of blood glucose levels in diabetic patients is essential to the proper management and treatment of the disease. The proper modulation of blood glucose by the administration of insulin, insulin analogs or oral hypoglycemic agents requires that multiple samples of blood be taken throughout each day. Existing diagnostic systems for the measurement of blood glucose are primarily based on the removal of a small sample of blood from the individual which is analyzed in a specialized device to determine and correlate blood glucose. As there may be considerable discomfort involved in obtaining the blood sample, patient compliance with treatment regimens is affected and effective treatment of the disease is impeded.

Consequently, multiple approaches have been examined to produce a relatively painless "non-invasive" glucose monitoring device. One approach has been to measure glucose levels in sweat which may be correlated to serum blood glucose. However, the concentrations of glucose in such samples is so low and fluctuates with environmental conditions that accurate correlation with blood glucose is difficult. However, the non-invasive aspects of this mode of measurement are sufficiently attractive to invite further study.

The concentration of glucose in a sample may be quantified electrochemically. Although glucose itself will not react selectively at a catalytic electrode surface to produce a measurable electrical effect, a cascade mechanism involving the enzyme glucose oxidase produces hydrogen peroxide which will react at an electrode surface to produce a measurable electrical current proportional to glucose concentration. Devices for the measurement of electrochemically significant quantities of analytes, such as glucose, extracted through the skin require electrodes of sufficient size and sensitivity to accommodate the extremely low concentration of glucose obtainable. Design of such electrodes is complicated by the inherent "noise" of the surrounding environment and the inherent electrical properties of the materials involved in producing such a device.

In an effort to increase the quantity of glucose obtained through the surface of the skin and to provide reproducibility in the quantity of fluid extracted through the skin surface, a glucose monitoring system has been proposed which is based on the active extraction of glucose through the surface of the skin by the process of "reverse iontophoresis." Reverse-iontophoresis is a process by which compounds are extracted through the surface of the skin by the application of an electrical field. Although charged species would be expected to move under the influence of the electric field, it has been found that uncharged species (such as glucose at physiological pH) will also co-migrate with the charged species. It has been determined that the quantity of glucose obtained by such methodology does correlate reproducibly to serum blood glucose measurements. Tamada, et al. (1995) Nature Medicine 1:1 198–1201. However, the quantity of glucose obtainable by such methodology remains substantially lower than the concentration of glucose in raw blood samples. Glucose is present in whole blood in a concentration of approximately 5 millimolar. In comparison, the concentration of glucose in fluid obtained as described in the system above is on the order of 2 micromolar to 100 micromolar. Consequently, conventional electrochemical systems for the measurement of blood glucose are not suitable for measurement of blood glucose in such concentrations.

Efforts to increase the quantity of glucose extracted have been described. Primarily, these methods have focused on increasing the permeability of the skin. Traditional chemical permeation enhancers such as PGML, (propylene glycol monolaurate) have been employed. Other methods known to increase skin permeability such as electroporation and ultrasound have also been employed. A device for the transcutaneous measurement of glucose having a two-chamber system is described in U.S. Pat. No. 5,362,307, issued Nov. 8, 1994 and U.S. Pat. No. 5,279,543, issued Jan. 18, 1994 the entire teachings of which are herein incorporated by reference. A modification to this system has been devised in which the polarity of the two electrodes is periodically reversed resulting in enhanced extraction of glucose through the skin. (Tamada, et al. ibid.) The quantity of glucose obtained using the alternating polarity protocol enables a sufficient quantity of glucose to be extracted to be electrochemically measured. However, in order to enable the device to operate in the alternating polarity mode, each chamber must contain both a set of sensing electrodes and an iontophoretic electrode. The inclusion of both sensor and iontophoretic electrodes in each chamber limits the size of each electrode based on spatial limitations. Furthermore, the inclusion of both iontophoretic and sensing electrodes in each chamber adds to the complexity and cost of the device.

SUMMARY OF THE INVENTION

The present invention provides an electrode assembly for use in a transdermal analyte sensor operating in an alternating polarity mode in which a single electrode element provides both the sensor counter electrode and iontophoretic electrode functions. By combining both the functions of the iontophoretic and counter electrode, the surface area of the electrode with respect to each function may be made larger. In turn this increases the ability of the electrode to deliver the required electrical current over a larger area when operating in the iontophoretic mode as well as increasing the ability of the counter electrode to compensate for the larger sensing electrode facilitated by this new design. Another advantage is that the bi-modal electrode assembly is more easily and economically produced when compared to the preparation of an electrode element having independent electrodes achieving the iontophoretic electrode and counter electrode functions. A further object of the present invention provides an electrode assembly which is readily connected and disconnected from a power source and monitoring device, thus allowing for replacement of the electrode assembly, electrode subassembly, and/or an ionically conductive material (e.g., an electrolytic gel) used with the electrode assembly.

These and other objects, advantages and features of the present invention will become apparent to those persons skilled in the art upon reading the details of the composition, components and size of the invention as set forth below reference being made to the accompanying drawings forming a part hereof wherein like numbers refer to like components throughout.

DEFINITIONS

Figure 1:
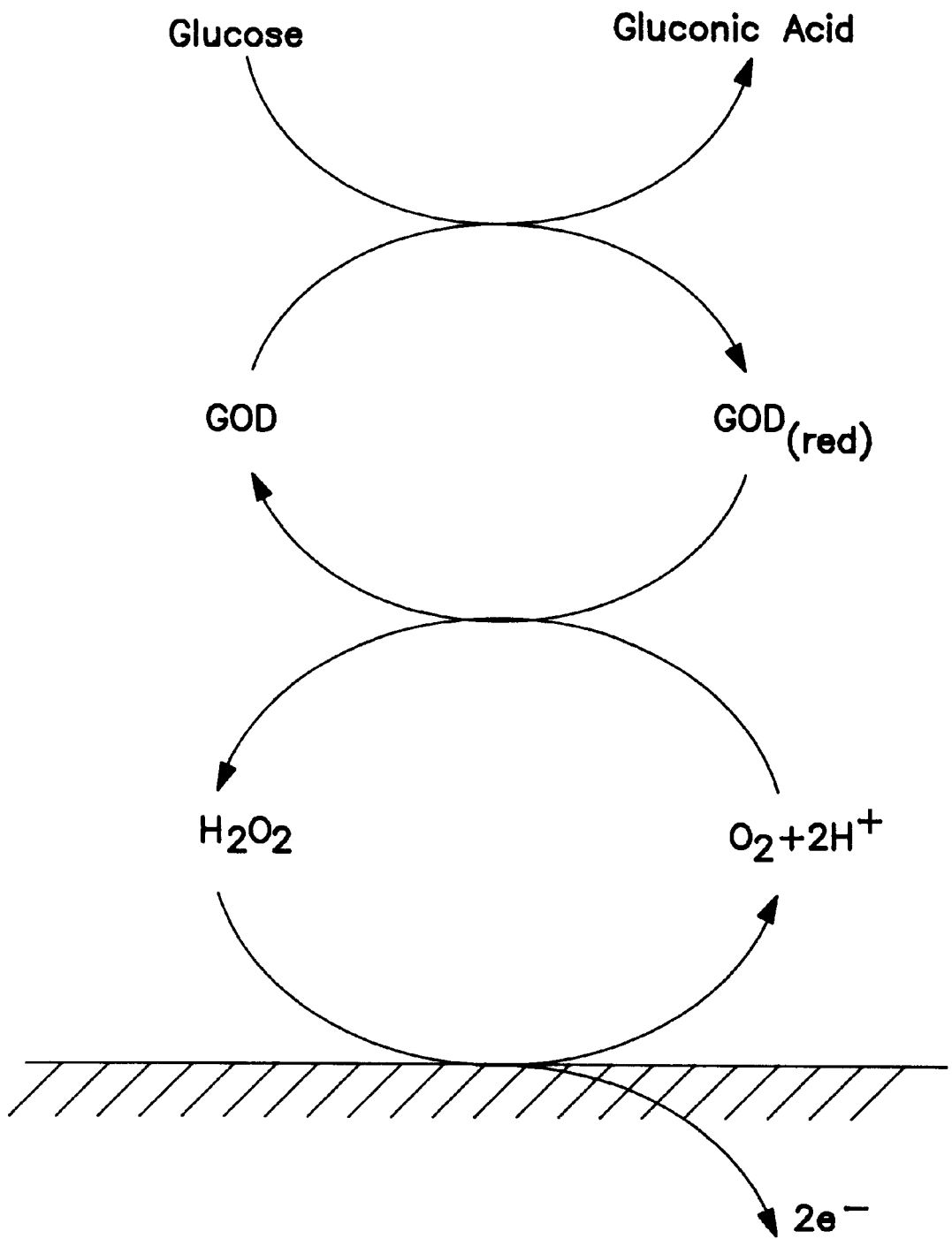
FIG. 1 is a schematic representation of the reaction which glucose oxidase (GOx) catalyzes to produce gluconic acid and hydrogen peroxide; hydrogen peroxide is then electrochemically reduced at the sensing electrode, thereby producing two electrons in the sensing circuit.

The term "bi-modal electrode" refers to an electrode which is capable of functioning non-simultaneously as both a counter electrode and a iontophoretic electrode.

The term "catalytic surface" or "catalytic face" are used interchangeably herein to mean the surface of the sensing electrode that is in contact with the surface of an electrolyte containing material through which the chemical signal flows from a source of chemical signal and is comprised of a catalytic material, e.g. platinum, palladium, or nickel and/or oxides, dioxides and alloys thereof). The catalytic surface catalyzes the conversion of the chemical signal into an electrical signal (i.e., an electrical current); and defines the electrode surface area that, when composed of a catalytic material, is sufficient to drive the electrochemical reaction at a rate sufficient to generate a detectable, accurate electrical signal that is able to be correlated with the amount of chemical signal present in the electrolyte. Only that electrical signal generated at the catalytic surface of the sensing electrode is correlated with the amount of chemical signal present in the electrolyte.

The term "chemical signal," "electrochemical signal," or "electrochemical compound" are used interchangeably and mean the chemical compound that is ultimately converted to an electrical signal at the catalytic faces of the electrode subassembly. "Chemical signals" can be: 1) directly converted into an electrical current by chemical reaction at the catalytic face of the electrode assembly; or 2) indirectly converted into an electrical signal by the action of one or more catalysts. For example, in one embodiment of a transcutaneous iontophoretic diagnostic system, the chemical signal glucose is indirectly converted into an electrical signal by reactions driven by two catalysts. A first catalyst glucose oxidase (GOx), which is present in the electrolyte containing material (e.g., a hydrogel patch), converts glucose into gluconic acid and hydrogen peroxide. Hydrogen peroxide is then converted to a measured electrical current upon electrochemical reduction by platinum (the second catalyst) on the catalytic face of the sensing electrode.

The term "counter electrode" is used to mean an electrode in an electrochemical circuit which acts as a current source or sink to complete the electrochemical circuit. Although it is not essential that a counter electrode be employed where a reference electrode is included in the circuit and capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

The term "electrode" as employed herein is used in its conventional sense to refer to a component of an electrochemical cell in contact with an electrolyte through which current can flow by electronic movement. Electrodes, which are essential components of both galvanic (current producing) and electrolytic (current using) cells, can be composed of a number of electrically conductive materials, e.g., silver, lead, zinc, aluminum, copper, iron, nickel, mercury, graphite, gold, or platinum, and oxides, dioxides and alloys thereof.

The term "electrolyte" as employed herein is used in its conventional sense as any substance that provides ionic conductivity, and through which electrochemically active species can diffuse. Electrolytes can be solid, liquid, or semi-solid (e.g., in the form of a gel). Common electrolytes include sulfuric acid and sodium chloride, which ionize in solution. Electrolytes used in the medical field generally have a pH which is sufficiently close to that of the tissue in contact with the electrode (e.g., skin) so as to avoid injury to the tissue in which it is in contact. Electrochemically active species that are present in the electrolyte can undergo electrochemical reactions (oxidation or reduction) at the surface of the electrode. The rate at which the electrochemical reactions take place is related to the reactivity of the species, the electrode material, the electrical potential applied to the electrode, and the efficiency at which the electrochemically active species is transported to the electrode surface.

The term "electroosmotic electrode" or "iontophoretic electrode" as employed herein is defined as an electrode to which current is applied in sufficient quantity to effect the reverse-iontophoretic extraction of chemical signals through mammalian skin.

The term "ionically conductive material" means a material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage of electrochemically active species, especially the chemical signal of interest, through it.

The term "iontophoresis" generally refers to the movement of ionic species under the influence of an electrical field. The term is generally associated with the delivery of ionic drug compounds through the surface of the skin and is well known in the art (see e.g. U.S. Pat. No. 4,752,285 issued Jun. 21, 1988).

The term "reverse iontophoresis" or "electroosmosis" is understood in the art to refer to the extraction of compounds through the skin by the application of an electrical field to the surface of the skin. The technique of reverse iontophoresis is well known in the art. For example. Benjamin, et al. ((1954) J. Appl. Physiol. 6:401) describe the use of reverse iontophoresis to extract ionic species ($Na^+$, $K^+$) through the surface of the skin. Other applications of reverse iontophoresis to the extraction of various analytes through the surface of the skin are described in Glikfeld, et al. (1989) Pharma. Res. 6(11):988.; Shaya, et al. (1978) Medical and Biological Engineering and Computing 16(2):125; Burnette, R. and Marrero, D. (1986) J. Pharm. Sci. 75(8):738.

As used herein, "surface area" means the geometric surface area (e.g., the geometric surface area of a circular electrode defined by the formula $\pi r^2$), without accounting for microscopic surface roughness that can contribute to the actual, three-dimensional surface area. The microscopic surface area is important in considering the actual, three-dimensional surface area available to, for example, drive the electrochemical conversion of the chemical signal to an electrical signal.

The term "transcutaneous reverse-iontophoretic diagnostic system" as used herein describes an analytical device which measures the concentration of chemical signals extracted through the surface of the skin by reverse-iontophoresis. The aforementioned publications describe the use of this methodology to measure various analytes. In one embodiment of the device as exemplified herein is a transcutaneous reverse-iontophoretic diagnostic system is a system for the measurement of glucose. The general operation of a transcutaneous reverse-iontophoretic diagnostic system is the cyclical repetition of two phases: (1) a reverse-iontophoretic phase followed by a (2) sensing phase. During the reverse iontophoretic phase, current is applied to the iontophoretic electrode to induce the transcutaneous migration of the chemical signal into the first reservoir. At the end of the reverse iontophoretic phase, current is turned off to the iontophoretic electrode. This is followed by a sensing phase wherein the chemical signal reacts catalytically on the catalytic face of the first sensing electrode while at the second counter electrode, electrons generated at the first sensing electrode are consumed. In one embodiment of the device as exemplified herein is a transcutaneous reverse-iontophoretic diagnostic system is a system for the measurement of glucose.

The term "sensing electrode" means the electrode which is monitored to determine the amount of electrical signal generated at the electrode by the catalytic reaction of the chemical signal, which is then correlated with the amount of a chemical compound present in the electrolyte. The sensing electrode comprises a catalytic surface which catalyzes the conversion of chemical signal to electrical signal which surface is comprised of a material selected from the group consisting of platinum, palladium, nickel, carbon, noble metals (e.g., gold), and oxides, dioxides and alloys thereof.

DETAILED DESCRIPTION OF THE INVENTION

Before the electrode configuration of the present invention is described and disclosed it is to be understood that this invention is not limited to the particular components or composition described as such may, of course, vary. It is also to be understood that the terminology used herein is for the purpose of describing particular embodiments only, and is not intended to be limiting since the scope of the present invention will be limited only by the appended claims.

The instant invention is shown and described herein in what is considered to be the most practical, and preferred embodiments. It is recognized, however, that departures may be made therefrom which are within the scope of the invention, and that modifications will occur to one skilled in the art upon reading this disclosure.

It must be noted that as used in this specification and the appended claims, the singular forms "a", "an" and "the" include plural referents unless the context clearly dictates otherwise. Thus, for example, reference to "a molecule" includes a plurality of molecules and different types of molecules.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described.

The present invention is useful in connection with the detection of biologically significant molecules such as glucose which are moved through human skin using a technique known as electroosmosis. The basic concept of moving a molecule such as a glucose through human skin is disclosed within U.S Pat. No. 5,362,307, issued Nov. 8, 1994 and U.S. Pat. No. 5,279,543, issued Jan. 18, 1994.

The present invention provides an electrode assembly for use in a transcutaneous reverse-ionotophoresis diagnostic system wherein said assembly comprises:

(a) a first and second bi-modal electrodes;

(b) a first and second sensing electrodes;

(c) a substrate;

wherein the bi-modal electrodes and sensing electrodes are substantially co-planar. In the preferred practice of the invention, the catalytic face of each sensing electrode comprises a platinum catalytic surface and the bi-modal electrodes are comprised of Ag/AgCl. Preferably, the sensing electrode operates at a current level in the range of 1 nanoamp to 1 milliamp and the bi-modal electrode operates at a current level in the range of 1 nanoamp to 5 milliamps.

The present invention further provides a method of determining the concentration of an analyte in a mammalian subject using a trancutaneous reverse-ionotophoresis diagnostic system, said method comprising the steps of:

(a) contacting a first surface of an ionically conductive hydrogel comprising water, electrolyte and an enzyme with skin of the mammalian subject and contacting a bi-modal electrode assembly to a second surface of the hydrogel, the assembly comprising a first and second bi-modal electrodes, a first and second sensing electrodes and a first and second reference electrodes;

(b) for a fixed period of time, providing a current to the first bi-modal electrode in an amount sufficient to effect the reverse-iontophoretic extraction of a chemical signal through the mammalian subject's skin, through the hydrogel and to the catalytic surface of the first sensing electrode;

(c) for a second period of time, providing a potential to the first sensing electrode in an amount sufficient to drive electrochemical conversion of chemical signal while utilizing the second bi-modal electrode as a counter electrode with respect to the first sensing electrode;

(d) measuring the electrical current generated by the electrochemical conversion at the electrode; and (e) correlating the measured current to a concentration of chemical signal in the mammalian subject.

In the preferred practice of the invention, the device operates in an alternating polarity mode necessitating the presence of a first and second bi-modal electrodes and two collection reservoirs. In the present invention, each bi-modal electrode serves two functions depending on the polarity of the operation as both: (1) an electroosmotic electrode used to electrically draw electrochemical compounds from a source into a collection reservoir comprising water and an electrolyte, and to the area of the electrode subassembly and (2) as a counter electrode to the first sensing electrode at which the chemical compound is catalytically converted at the face of the sensing electrode to produce an electrical signal.

Current is supplied to both the reference and sensing electrodes as well as to the bi-modal electrode. In general, practical limitations of the system require that the bi-modal electrode will not act as both a counter and iontophoretic electrode simultaneously. However, alternate or simultaneous supply of current to the electroosmotic and sensing electrodes does not affect the calculation of the peroxide flux at the sensing electrode catalytic face.

The general operation of a transcutaneous reverse-iontophoretic diagnostic system is the cyclical repetition of two phases: (1) a reverse-iontophoretic phase followed by a (2) sensing phase. During the reverse iontophoretic phase, the first bi-modal electrode acts as an iontophoretic electrode and the second bi-modal electrode acts as a counter electrode to complete the circuit. At the end of the reverse iontophoretic phase, current is turned off. During the sensing phase, the chemical signal reacts catalytically on the catalytic face of the first sensing electrode while the second bi-modal electrode acts as a counter electrode at which electrons generated at the first sensing electrode are consumed.

The electrode described is particularly adapted for use in conjunction with a hydrogel collection reservoir system for monitoring glucose levels in a subject through the reaction of collected glucose with the enzyme glucose oxidase present in the hydrogel matrix. The general principle for the enzymatic measurement of glucose concentration utilizing glucose oxidase is based on the following series of reactions:

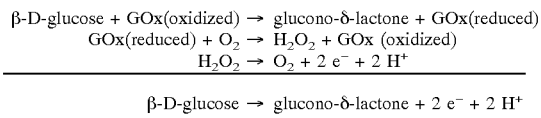

An electroosmotic electrode (e.g., iontophoresis or reverse iontophoresis electrodes) can be used to electrically draw glucose into the hydrogel. Glucose oxidase (GOx) contained in the hydrogel converts the glucose into gluconic acid and hydrogen peroxide. The hydrogen peroxide produced reacts at the catalytic face of a platinum electrode to produce a measurable electrical signal. This system allows for the continuous and accurate measurement of an inflow of a very small amount of glucose in an electrolyte (e.g., glucose concentrations 10, 500, or 1,000 or more times less than the concentration of glucose in blood). A feature of the electrode subassembly of the invention is that it is small, flat, and thin, having a total surface area in the range of about 0.1 cm$^2$ to 10.0 cm$^2$, and a thickness in the range of about 0.25 $\mu$m to 250 $\mu$m. The concept of converting the very small amounts of molecules such as glucose which can be extracted through the skin in order to create a current by use of glucose oxidase is disclosed within earlier filed application Ser. No. 08/265,844, filed Jun. 24, 1994 and application Ser. No. 08/373,931, filed Jan. 10, 1995; and hydrogel patches suitable for use with the present invention are disclosed within earlier filed application Ser. No. 08/501,664, filed Jul. 12, 1995, each of which applications are incorporated herein by reference in their entirety and which applications disclose inventions which were invented under an obligation to assign rights to the same entity as which the rights in the present invention were invented under an obligation to assign to.

Figure 2:
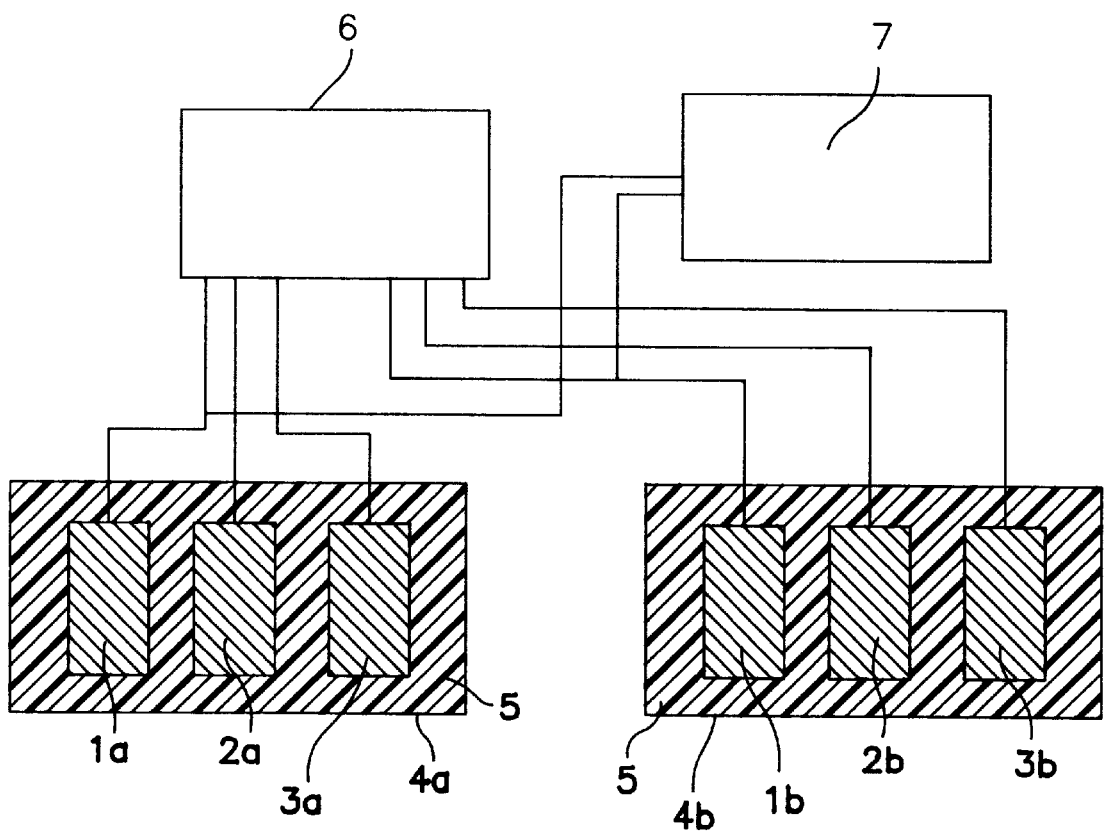
FIG. 2 is a schematic of an operating circuit for the electrode subassembly (4) of the invention comprising bi-modal electrodes 1a and 1b, sensing electrodes 2a and 2b, reference electrodes 3a and 3b, substrate (5), potentiostats (6) and an iontophoretic power supply (7).
Figure 3:
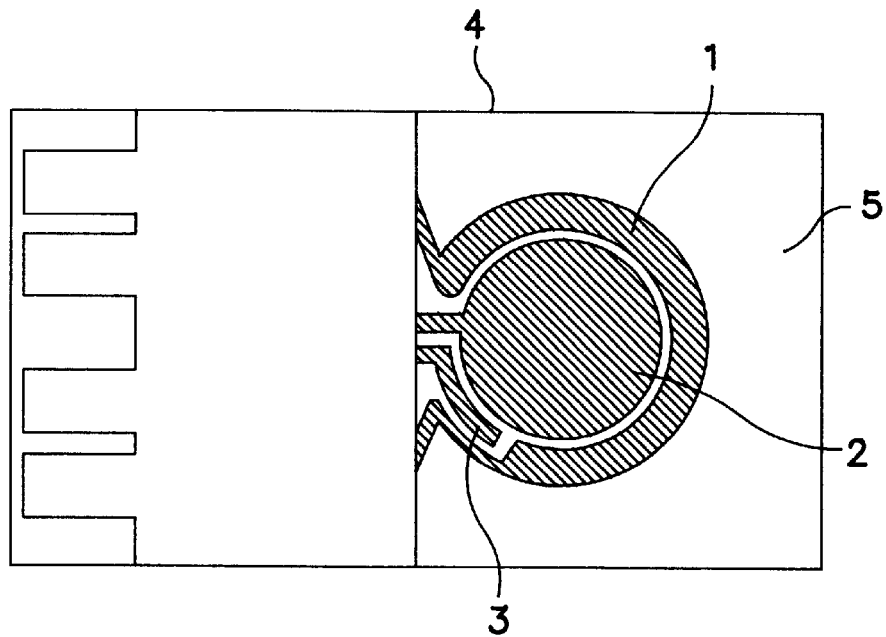
FIG. 3 an overhead and schematic view of the electrode assembly (4) comprising a bi-modal electrode (1), a sensing electrode (2), and a reference electrode (3) mounted on a substrate (5).
Figure 4:
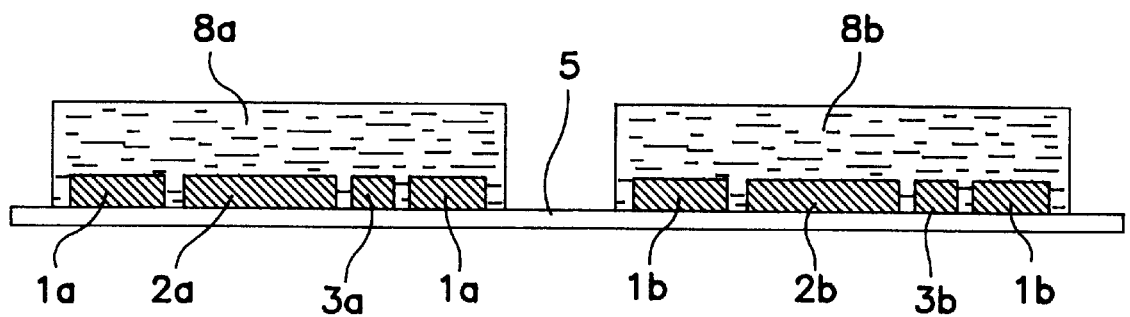
FIG. 4 is a cross-sectional schematic view of the bi-modal electrodes as they may be used in conjunction with reference electrode and a hydrogel patch comprising bi-modal electrodes 1a and 1b, sensing electrodes 2a and 2b, reference electrodes 3a and 3b, substrate (5), and hydrogel pads 8a and 8b.

The monitoring of a chemical signal diffused through a surface can be accomplished using a single electrode assembly of the invention. However, in a preferred embodiment of the invention as described above, an electrode assembly comprising two bi-modal electrodes and two sensing electrodes, each pair of sensing and bi-modal electrodes being positioned on adjacent, electrically isolated electrolyte surfaces, are used to monitor the chemical signal. FIG. 2 is a schematic view of an exemplary embodiment of the electrode subassembly of the invention. The basic structural components of the electrode subassembly are a substrate, two sensing electrodes and two bi-modal electrodes. The electrodes are in substantially the same plane, and are of substantially the same thickness. Each bi-modal electrode (1$a$, 1$b$) and each sensing electrode (2$a$,2$b$) is connected by leads to a power source and monitoring device for generating an electric current through the electrodes and a monitoring device for measuring the electric current generated at the sensing electrode.

A. Substrate:

The substrate is composed of an electrically insulating material onto which the conductive material of the electrode is coated. The substrate can be composed of any insulating material (e.g., a ceramic, plastic (e.g., polyethylene, polypropylene), or polymeric material) to which the electrode assembly can be affixed. Preferably, the electrode assembly is affixed to an electrically insulating plastic or ceramic substrate, generally having a thickness of approximately 100 $\mu$m to approximately 3 mm. The substrate should be of sufficient thickness and stability to insure sufficient structural integrity such that it can be readily handled by human fingers without significant handling difficulties. In the preferred practice of the invention, the substrate material is an electrically insulating ceramic.

B. Electrode Size

The relative size (i.e., diameter, surface area, thickness, etc.) of the bi-modal electrodes can vary according to a variety of factors, including the dimensions of the surface through which the chemical signal is to be detected (e.g., the size of a hydrogel patch through which the chemical signal is drawn), or the size constraints of a monitoring electrode assembly used in connection with the electrode subassembly. The sensing electrodes are normally quite thin, with an average thickness in the range of 0.25 $\mu$m to 250 $\mu$m.

In general, the size of the bi-modal electrode will vary according to a variety of factors, e.g. the thickness of a ionically conductive material (e.g., hydrogel patch) used with the electrode assembly, the diffusion characteristics of the chemical signal to be detected by the electrode subassembly for a given geometry, and the duration of the sensing period (i.e., monitoring period). For example, where the electrode assembly is used with an electrolytic hydrogel patch having a thickness in the range of about 100 μm to 700 μm, the bi-modal electrode will preferably have a surface area of approximately 1 cm$^2$, preferably greater than 0.75 cm$^2$. In general, as the thickness of the ionically conductive material and the area of the electrode are directly correlated (e.g., the thicker the gel, the greater the surface area of the electrode). In a preferred embodiment, the ionically conductive material is from about 5 mil to 30 mil thick and the electrode has a surface area of approximately 1.3 cm$^2$. Where the electrode assembly is used in connection with an ionically conductive material (e.g., a hydrogel patch), the surface area of the electrode assembly is less than the surface area of the ionically conductive material. In general, the surface area of the ionically conductive material for use with the electrode assembly and electrode subassembly of the invention range from about 0.5 cm$^2$ to about 10 cm$^2$, preferably about 1 cm$^2$ to about 5 cm$^2$.

Preferably, the electrodes will optimally operate at a pH which is relatively close to that of the solid or electrolyte in which the electrode subassembly is in contact (e.g, human skin (about 7), hydrogel patch) and at least within a range of from about pH 4 to pH 9. In general, the electrodes operate at a current level in the range of 1 nanoamp to 1 milliamp.

C. Bi-Modal Electrode Material

The bi-modal electrode is preferably comprised of Ag/AgCl. The electrochemical reaction which occurs at the surface of this electrode:

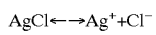

serves as a rapid facile source or sink of electrical current. This property is especially important for the iontophoresis function of the electrode. Lacking this reaction, the iontophoresis current would cause the hydrolysis of water to occur at the iontophoresis electrodes causing pH changes and possible gas bubble formation. The pH changes to acidic or basic pH could cause skin irritation or burns. The ability of an Ag/AgCl electrode to serve as a source or sink of current is also an advantage for its counter electrode function. For a three electrode chemical cell to function properly, the current generation capacity of the counter electrode must not limit the speed of the reaction at the sensing electrode. The case of a large sensing electrode, the ability of the counter electrode to source proportionately larger currents is required.

The design of present invention provides for a larger sensing electrode than previously designed. Consequently, the size of the bi-modal electrode must be sufficient so that when acting as a counter electrode with respect to the sensing electrode the counter electrode does not become limiting of rate of catalytic reaction at the sensing electrode catalytic surface. Two methods exist to ensure that the counter electrode does not limit the current at the sensing electrode: (1) make the bi-modal electrode much larger than the sensing electrode, or (2) provide for a facile counter reaction to occur.

E. Sensing Electrode Material

Preferably, both sensing electrodes are comprised of the same catalytic material on their catalytic surfaces, preferably Pt, PtO and/or PtO$_2$. The catalytic surface of the bi-modal electrodes is the face of the electrode in contact with the electrolyte (e.g., a hydrogel patch) and which is responsible for conversion of chemical signal to electrical signal, and thus the face which constitutes the minimal portion of the electrode that must be composed of the catalytic material. The catalytic material of the catalytic surface is the material that promotes conversion of the chemical signal into an electrical signal. Exemplary catalytic materials include carbon as well as platinum, palladium, gold, iridium, or other noble metal. Where the chemical signal to be detected is hydrogen peroxide (e.g., generated by catalysis of glucose by GOx), the preferred catalytic materials on the catalytic surfaces of the sensing and scavenging electrodes are platinum, palladium, iridium, or other noble metal, more preferably platinum or oxides, dioxides or alloys thereof.

The bi-modal electrodes can be porous or non-porous, preferably non-porous. The electrodes can be made of a single catalytic material (e.g., stamped from a thin sheet of platinum). Alternatively, the electrodes can be plated (e.g., electrolytic or non-electrolytic plating), coated, printed, photolithographically deposited, or otherwise affixed to a substrate using methods well known in the art for application of a thin metal layer on a surface.

The sensing electrodes can have the catalytic material over all electrode surfaces. Alternatively, only the catalytic faces of the electrode subassembly have the catalytic material. Preferably, the catalytic material is platinum or a platinum-containing material which is present on at least the catalytic surface of the sensing electrodes.

F. Electronics

During the reverse iontophoretic phase, the power source provides a current flow to the first bi-modal electrode to facilitate the transcutaneous extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintain a fixed potential at the electrode where, for example, hydrogen peroxide is converted to molecular oxygen, hydrogen ions, and electrons, which is compared with the potential of the reference electrode (3) during the sensing phase. While one sensing electrode is operating in the sensing mode it is electrically connected to the other bi-modal electrode which acts as a counter electrode at which electrons generated at the sensing electrode are consumed. FIG. 2 illustrates an example of an operating circuit using bi-modal (1a and 1b), sensing (2a and 2b) and reference (3a and 3b) electrodes with an iontophoretic power source (7) and monitoring device (6).

The electrode sub-assembly can be operated by electrically connecting the bimodal electrodes such that each electrode is capable of functioning as both an electro-osmotic electrode and a counter electrode along with appropriate sensing electrode(s) and reference electrode(s), to standard potentionstat circuitry. A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentionstat circuits can be used to operate the two biosensors. For the purpose of the present invention, the electrical current measured at the sensing electrode subassembly is the current that is correlated with an amount of chemical signal.

G. Monitoring Device

In order to facilitate the communication of the concentration of chemical signal measured to the patient, it is desirable to include a device capable of converting the electrical signal produced at the sensing electrode into a visual signal. Examples of such monitoring devices capable of communicating the magnitude of an electrical signal to an operator include galvanometers incorporating analog or digital displays and are well known in the art. In the preferred practice of the invention, the monitoring device consists of a programmed digital computer incorporating a digital display, said computer being programmed with an algorithm appropriate to convert the raw electrical signal produced at the sensing electrode to a numerical display of the correlative subcutaneous concentration of the chemical signal.

H. Design Considerations

Mechanically the electrode assembly will have sufficient structural integrity such that it can be readily handled by human fingers without significant handling difficulties or significantly compromising the performance of the electrode. Further, where the electrode assembly is used in conjunction with an ionically conductive material (e.g., a hydrogel patch), it may be desirable to remove the material from the electrode. Thus, it may be desirable to design the electrode so that the patch can be removed from the electrode assembly and electrode subassembly without significantly degrading the surface of the electrodes, or adhering to the electrodes in a manner that makes it difficult to completely remove all patch material from the face of the electrodes. The electrode subassembly and/or electrode assembly can be provided as a unit separate from the any other component of a monitoring device (e.g., a glucose monitoring device). Alternatively, the ionically conductive material and the electrode subassembly and/or electrode assembly can be provided as a single unit.

The electrode assembly and/or electrode subassembly can include additional materials that enhance the performance, handleability, and/or durability of the electrode assembly and/or electrode subassembly. For example, the electrodes can be coated with a material that serves to decrease the interference of other species in the electrolyte with the measurement of electric current at the sensing electrode. Preferably, the electrode assembly is manufactured in a manner that is the most economical without compromising electrode performance (e.g, the ability of the electrodes to catalyze the chemical signal, and/or conduct an electrical current, or the ability to manipulate the electrodes by hand without breaking or otherwise compromising the operability of the electrodes).

Based on the description above and in the figures, it will be recognized that the electrode subassembly and electrode assembly of the invention can be configured in a variety of different forms, and from a variety of different materials. However, the electrodes will have certain defined mechanical, electrical, chemical and diffusion characteristics.

For reasons that may relate to factors such as the build up of undesired materials in the electrode assembly, the electrode assembly should be easily replaceable (e.g., by a patient) in a convenient manner. In general, the electrode assembly is designed for use in continuous chemical signal sensing over a period ranging from about 1 day to 1 week, preferably about 1 week to 2 weeks, more preferably about 2 weeks to 4 weeks or more. After such time, the electrode is preferably designed so that it is disposable (e.g., can be readily detached from the monitoring device and replaced with a new electrode subassembly and/or electrode assembly). Accordingly, the electrode assembly must have some structural integrity, and provide for the detection of the chemical signal of interest. In that the electrode assembly and sensor housing containing the electrode assembly is preferably small (e.g., hand held, e.g., the size of a watch to be worn on the wrist of a patient), it is necessary that the electrode assembly and electrode subassembly be particularly thin, e.g., in the range of 0.25 µm to 250 µm. In order to accurately measure the amount of a chemical signal (e.g., the amount of hydrogen peroxide generated by GOx catalysis of glucose) and be sufficiently large to be manipulated, the electrode assembly cannot be too thin and cannot be too small.

We claim:

1. An integral electrode assembly for use in a transcutaneous reverse-iontophoresis diagnostic system wherein chemical signals are extracted through the surface of a patient's skin by application of an electrical field, said assembly comprising:
   (a) a pair of electrically connected iontophoretic electrodes adapted for applying electrical current to the skin to extract chemical signals therefrom;
   (b) a first sensing electrode positioned adjacent one of the iontophoretic electrodes for detecting the chemical signals extracted thereby;
   wherein the first sensing electrode is electrically connected with said iontophoretic electrode such that said iontophoretic electrode serves as a counter electrode therefor and defines a first sensor electrode pair.

2. The electrode assembly of claim 1 further comprising a second sensing electrode positioned opposite the first sensor electrode pair and adjacent the remaining iontophoretic electrode for detecting the chemical species extracted thereby, wherein the second sensing electrode is electrically connected to the adjacent iontophoretic electrode such that said iontophoretic electrode serves as a counter electrode therefor and defines a second sensor electrode pair.

3. The electrode assembly of claim 2 wherein the iontophoretic and sensing electrodes are located upon a planar substrate.

4. The electrode assembly of claim 3 wherein the substrate comprises a polymeric or ceramic material.

5. The electrode assembly of claim 4 wherein the substrate is a plastic film.

6. The electrode assembly of claim 2 further comprising a first and second reference electrode positioned adjacent to the first and second sensor electrode pairs, respectively.

7. The electrode assembly of claim 2 further comprising a first ionically conductive material having a first surface adapted to contact the surface of the skin and a second surface opposite the first surface which is in contact with the first sensor electrode pair.

8. The electrode assembly of claim 7 further comprising a second ionically conductive material having a first surface adapted to contact the surface of the skin and a second surface opposite the first surface which is in contact with the second sensor electrode pair.

9. A method of determining the concentration of a chemical signal in a mammalian subject using the transcutaneous reverse-iontophoresis diagnostic system of claim 22, said method comprising the steps of:
   (a) contacting the first surfaces of the first and second ionically conductive materials to the skin of the mammalian subject;
   (b) providing a current between the iontophoretic electrode pair to extract the chemical signal through the skin and into the first ionically conductive material;

(c) providing a potential between the first sensor electrode pair sufficient to drive an electrochemical conversion of the chemical signal contained within the first ionically conductive material and measuring the electrical current generated by this electrochemical conversion of chemical signal; and (d) correlating the measured current in step (c) to a concentration of chemical signal in the subject.

10. The method of claim 9 wherein after step (d) the method further comprises the steps of:

(e) switching the polarity between the iontophoretic electrode pair and providing current to extract the chemical signal through the skin and into the second ionically conductive material;

(f) providing a potential between the second sensor electrode pair sufficient to drive an electrochemical conversion of the chemical signal contained within the second ionically conductive material, and measuring the electrical current generated by this electrochemical conversion of the chemical signal; and (g) correlating the measured current of step (f) to a concentration of chemical signal in the subject.

11. The method of claim 10 wherein the chemical signal is glucose and wherein the ionically conductive material is a hydrogel comprising water, glucose oxidase and an electrolyte.

12. The method of claim 9 wherein the sensing electrodes include a platinum containing catalytic surface and the iontophoretic electrodes are comprised of Ag/AgCl.

13. The method of claim 9 wherein the first sensor electrode pair is operated at a current level in the range of 1 nanoamp to 1 milliamp and the iontophoretic electrode pair are operated at a current level in the range of 1 nanoamp to 5 milliamps.

14. The electrode assembly of claim 7 wherein the ionically conductive material comprises a hydrogel.

15. The electrode assembly of claim 14 wherein the hydrogel comprises water, glucose oxidase and an electrolyte and wherein the chemical signal is glucose.

16. The electrode assembly of claim 1 wherein the first sensing electrode comprises a platinum containing catalytic surface and the iontophoretic electrodes are comprised of Ag/AgCl.

17. The electrode assembly of claim 1 wherein the first sensor electrode pair operate at a current level in the range of 1 nanoamp to 1 milliamp and the iontophoretic electrode pair operate at a current level in the range of 1 nanoamp to 5 milliamps.

18. The electrode assembly of claim 1 further including a monitoring device.

* * * * *

UNITED STATES PATENT AND TRADEMARK OFFICE
CERTIFICATE OF CORRECTION

PATENT NO.   : 5,954,685
DATED        : September 21, 1999
INVENTOR(S)  : Michael J. Tierney It is certified that error appears in the above-identified patent and that said Letters Patent is hereby corrected as shown below:

<u>Column 12,</u>
Line 60, "claim 22" should be -- claim 8 --.

Signed and Sealed this

Twenty-second Day of October, 2002

Attest:

Attesting Officer

JAMES E. ROGAN
Director of the United States Patent and Trademark Office